United States Patent [19]
Jones et al.

[11] Patent Number: 5,188,655
[45] Date of Patent: Feb. 23, 1993

[54] PLANT GROWTH ENHANCING COMPOSITIONS USING GIBBERELLINS, INDOLEACETIC ACID AND KINETIN

[76] Inventors: Travis R. Jones, 3244 Southern, Memphis, Tenn. 38111; E. Robert Gates, 6381 Massey Hill, Memphis, Tenn. 38119

[21] Appl. No.: 446,012

[22] Filed: Nov. 2, 1989

Related U.S. Application Data

[63] Continuation-in-part of Ser. No. 146,484, Jan. 21, 1988, abandoned.

[51] Int. Cl.$^5$ ...................... A01N 43/08; A01N 43/38
[52] U.S. Cl. ....................................... 504/136
[58] Field of Search ................................ 71/92, 89, 96

[56] References Cited

U.S. PATENT DOCUMENTS

| | | | |
|---|---|---|---|
| 3,038,794 | 6/1962 | Geary et al. | 71/96 |
| 4,507,144 | 3/1985 | Aloni | 71/89 |

FOREIGN PATENT DOCUMENTS

| | | | |
|---|---|---|---|
| 6003651 | 2/1976 | Japan | 71/89 |
| 609525 | 6/1977 | U.S.S.R. | 71/89 |

OTHER PUBLICATIONS

Looney et al., "Promotion of flowering in apple trees etc.", 104:64082b 1986.
Rogózinska et al., "Induction of differentiation etc." CA 89:192371d, (1978).

*Primary Examiner*—Glennon H. Hollrah
*Assistant Examiner*—B. Bembenick
*Attorney, Agent, or Firm*—Richard C. Litman

[57] ABSTRACT

A plant growth enhancing composition comprising as an active ingredient a synergistic mixture of (a) gibberellins, (b) the heteroauxin indole-3-acetic acid and the cytokinin 6-(4-hydroxy-3-methyl-2-trans-betenylamino) purine in definite proportions. Application of the composition to the locus of various plants or to the seeds of a plant produces a wide variety of plant growth enhancing responses including, increasing yields; stimulating seed germination and breaking of dormancy; increasing flowering and fruiting; preventing lodging and freeze injury; aiding in the recovery of damaged crops and increasing root proliferation.

13 Claims, No Drawings

PLANT GROWTH ENHANCING COMPOSITIONS USING GIBBERELLINS, INDOLEACETIC ACID AND KINETIN

CROSS-REFERENCE TO RELATED APPLICATION

This application is a continuation-in-part of prior copending application Ser. No. 146,484, filed Jan. 21, 1988 and entitled "Growth Enhancing Compound" (now abandoned).

BACKGROUND OF THE INVENTION

1. Field Of The Invention

The present invention relates to novel plant growth enhancing compositions for stimulating various plant growth responses. More particularly, the invention relates to the use of plant growth enhancing compositions comprising a mixture of phytochemicals consisting of gibberellins, an auxin and a cytokinin for application to seed or foliage in order to stimulate seed germination or increase the overall development and yield of a variety of plant species.

2. Description Of The Prior Art

The growth and productivity of cultivated plants are known to be enhanced with the use of various growth stimulators. For example, there are known growth stimulators based on naturally occurring and synthetic auxins, such as indoleacetic acid and naphthaleneacetic acid, which induce stem elongation and promote root formation. Other synthetic auxins include 4-chloro-2-methylphenoxyacetic acid (MCPA); 2,4-chlorophenoxyacetic acid (2,4D); 2,4,5-trichlorophenoxyacetic acid (2,4,5-T); 2-(4-chloro-2-methyl-phenoxy) propionic acid (CMPP); 4-(2,4-dichlorophenoxy) butyric acid (2,4-DB); 2,4,5-trichlorobenzoic acid (TBA); and 3,5-dichloro-2-methoxybenzoic acid (dicamba), for example. All the above acids are active in the form of their salts and esters, such as their sodium, potassium, ammonium, dimethylamine and ethanolamine salts, and their lower alkyl esters. Many of these synthetic auxins are being used commercially as effective herbicides and some of them are known to adversely effect morphogenesis of treated plants.

Preparations based on cytokinins, such as 6-furfurylamino purine and 6-benzlyamino purine, are also known to be growth stimulators. However, cytokinins-based preparations which have a decisive influence in the stimulation of cell division seldom produce a desirable effect in the absence of auxins. While the mechanism by which cytokinins effect the growth cycle of plants is far from being understood, it is apparent that they affect leaf growth and prevent aging in certain plants. While the action of cytokinins on the growth of cultivated plants has been extensively studied, these plant hormones did not find wide application in plant raising since they must be applied at specific concentrations in parts per million. These critical rates of application render cytokinins-based preparations highly impractical in an agricultural environment.

Of all the known s mulators, the most widely used is a series of natural plant hormones generically named "gibberellins". The gibberellins are used for the acceleration or regulation of various stages of plant development, particularly growth, efflorescence, germination and parthenocarpy of higher plants. A series of related compounds identified as gibberellin $A_1$ through $A_{44}$ has been obtained by microbiological synthesis and the various compounds isolated from culture broth of *Gibberella fujikuroi* and from various plants including certain beans. The main component of the gibberellins used in practice is gibberellin $A_3$, otherwise known as gibberellic acid.

While the gibberellins are highly effective as plant growth promoting or regulating substances, their use is greatly limited by their expense and insufficient effectiveness at low concentrations. As a result, considerable research has concentrated on efforts to find synergistic agents which can be used to enhance the activity of the gibberellins. One such synergistic agent for use with the gibberellins that have been discovered and put to practical use is described in U.S. Pat. No. 4,507,144 to Aloni. This patent discloses a composition consisting of the auxin naphthaleneacetic acid (NAA) and gibberellic acid ($GA_3$) used for application to growing plants in order to increase the fiber content of the plants. However, the patented composition does not find wide application in plants other than those disclosed as being used as a source of commercial fibers and show little efficiency in stimulating growth, flowering and fructification of horticultural crops. Moreover, since the disclosed composition is applied to the plant as an aqueous spray, appreciably quantities of the composition flows down onto the soil and is not absorbed and assimilated in a systemic manner by the plant. Another disadvantage of the particular aqueous composition described by Aloni, which is especially specific when a spraying technique is employed, is the reduction of crop quality caused by the impossibility of attaining equally uniform application of the aqueous spray to various parts of the treated plant. A further disadvantage resides in the relatively high water requirements for the preparation of the reference compositions, the consumption of water being up to 800 liters per hectare.

The use of certain other gibberellin-based preparations in various forms for such specific applications as healing plant wounds, promoting flowering in apple trees and inducing plant growth in isolated sugar beet leaves is also known in the agricultural art. However, these known preparations do not find application over a wide range of crops and do not demonstrate a wide variety of plant growth enhancing properties.

There is, therefore, an urgent need for a growth enhancing composition consisting of synergistic agents for use with the gibberellins which enables a lower rate of application and displays a wide array of effects in the developmental processes of various agricultural and horticultural crops.

SUMMARY OF THE INVENTION

Accordingly, the principal object of the present invention is to provide a growth enhancing composition comprising a synergistic mixture of specific phytochemicals consisting of a gibberellin, an auxin and a cytokinin in definite proportions for wide application to various plant species in very specific rates in order to achieve a wide variety of plant growth enhancing responses.

It is a further object of the invention to provide a composition for plant growth enhancement comprising the above-mentioned synergistic mixture of phytochemicals in association with auxiliary nutrients, which sustain the plant for short periods of time during plant development and also serve as a vehicle whereby the synergistic mixture may be applied in a convenient and economical manner.

It is an additional object of the invention to provide a method of enhancing plant growth which comprises applying an effective amount of the plant growth enhancing composition comprising a synergistic mixture of phytochemicals consisting of gibberellins, an auxin and a cytokinin to a plant species or seed of a plant.

These and other objects are accomplished in accordance with one embodiment of the present invention by providing a growth enhancing composition comprising a synergistic mixture of:

(a) 35–45 percent by weight of gibberellins, (b) 35–45 percent by weight of the heteroauxin indole-3-acetic acid, and (c) 15–25 percent by weight of the cytokinin 6-(4-hydroxy-3-methyl-2-trans-betenylamino) purine.

The mechanism by which compositions of the present invention effect the growth cycle of plants is not fully understood at present, but it is apparent as will be demonstrated hereinafter that they play a significant role in inducing a number of growth enhancing responses in a variety of plant species. The term "growth enhancing" or the term "method of enhancing plant growth" or the use of the words "enhancer" or "enhancement" in the specification and claims mean a variety of plant responses which improve some characteristic of the plant as distinguished from herbicidal activity, the intention of which is to destroy or stunt the growth of the plant. For this reason the compositions used in the practice of the present invention are used in precise amounts which are non-phytotoxic with respect to the plant being treated.

By virtue of the practice of the present invention a wide variety of plant growth responses have been achieved, including stimulation of seed germination and breaking of dormancy; increasing yields; hastening ripening and color production in fruit; increasing flowering and fruiting; inducing rooting and causing cell proliferation; increasing the hardiness of various plant species; and increasing the dry weight content of a number of plants and plant parts. In addition to these categories of responses any other modification of a plant, seed, fruit or vegetable so long as the net result is to increase the growth or maximize any beneficial property of the agricultural and horticultural crop or seed as distinguished from herbicidal action is intended to be included within the scope of advantageous responses achieved by the practice of the present invention.

The above-mentioned types of growth enhancing responses can be produced on a variety of plant species when they are treated with the compositions of the invention. Suitably applied as a seed dressing, the present compositions have been shown to simulate the germination and terminate the dormancy of such crop seeds as wheat, oats, barley, cotton, beans and peanut, for example. The treated seeds were quicker to germinate and emerge considerably more quickly and evenly than untreated seeds. Also, the compositions repeatedly exhibited the ability of initiating dormancy break and causing root proliferation of plant seeds, even under adverse field conditions. In addition, suitable application of the growth enhancing compositions of the present invention to seeds has been shown to induce vigor resulting in stronger and firmer plants capable of resisting natural tenancies toward lodging and freeze injury. This effect has been observed on a number of plant species, such as wheat and barley, for example.

When suitably applied as a foliar cover spray in conjunction with a sulfur auxiliary nutrient carrier, the compositions of the present invention are capable of inducing rooting and causing cell proliferation as immediate responses by balancing sulfur/nitrogen ratios in many plants, including, but not limited to nitrogen-sensitive crops, such as cotton, rice, wheat and small grains, particularly, oats and barley. The net effect is a treated plant that more efficiently utilizes available nutrients from all sources. Also, the present compositions when suitably applied have been found to increase flowering and fruiting in a number of economic crops, such as soybeans, kidney beans and cotton, and are capable of measurably increasing the leaf area relative to the stem area in many plants. The increased ratio of leaves to the stem results in changing the biochemical composition of the treated plant.

Suitable application of the growth enhancing compositions of the present invention as a foliar cover spray has been shown to consistently increase yields of the order of 15–20% in a number of plant species, including wheat, oats and rice, for example. The economical advantages of consistent yield increases of this magnitude are evident. The present compositions may be applied at any developmental stage of the plant species and have been found to display plant hormone or maintenance effects throughout maturity and to expedite regrowth in damaged crops during early developmental stages, depending upon the concentration used, the formulation employed and the type of plant species treated.

The compositions of present invention are preferably used in conjunction with specific auxiliary nutrients or other plant growth stimulators in precise proportions to achieve a particular synergistic, growth enhancing response in various types of plants. The present compositions may additionally be used in association with fungicides to increase the disease resistance of various plants, making the plant tissue resistant to invasion by pathogens by influencing the enzyme and plant processes which regulate growth nature disease immunity. While the present compositions possess essentially no phytotoxic activity of their own, they may sometimes be used in conjunction with herbicides to stimulate the growth of unwanted plants in order to make such plants more susceptible to a herbicide. However, it is preferred to regard the results achieved in the practice of the present invention as growth enhancing responses in agricultural and horticultural crops, as well as perennial and annual household plant species.

The above description, as well as further objects, features and aspects of the present invention, will be more fully appreciated by reference to the following detailed description.

DETAILED DESCRIPTION OF THE INVENTION

The gibberellins employed as one of the phytochemical components of the growth enhancing composition of the present invention preferably comprise about 40% by weight of a mixture of gibberellic acids consisting essentially of gibberellin $A_2$ ($GA_2$), gibberellin $A_3$ ($GA_3$), gibberellin $A_5$ ($GA_5$), gibberellin $A_7$ ($GA_7$) and gibberellin $A_{14}$ ($GA_{14}$). The following mixture of gibberellic acids taken in the following specific proportions (% by weight) is especially preferred because of its high activity on various plants and ready availability:

| PREPARATION A | |
|---|---|
| $GA_2$ | 4 |

| PREPARATION A | |
|---|---|
| GA$_3$ | 76 |
| GA$_5$ | 4 |
| GA$_7$ | 4 |
| GA$_{14}$ | 12 |

The heteroauxin indole-3-acetic acid employed in the practice of the invention preferably comprises about 40% by weight of the present growth enhancing composition, with the remaining essential component being the cytokinin 6-(4-hydroxy-3-methyl-2-trans-betenylamino) purine (Zeatin) and preferably comprising about 20% by weight of the composition. An especially preferred growth enhancing preparation according to the present invention had the following chemical composition, wherein the components are listed as percent by weight:

| COMPOSITION 1 | |
|---|---|
| PREPARATION A | 40.3 |
| INDOLE-3-ACETIC ACID | 38.7 |
| ZEATIN | 21.0 |

The growth enhancing compositions according to the invention generally comprise the above active components mixed with a carrier or auxiliary nutrients. The auxiliary nutrients used in conjunction with the practice of the present invention are precursory in their role in that they furnish only minute portions of nutrients to the plant to sustain the plant for a very short period of time until the compositions used in the practice of the present invention are able to exert their growth enhancing activity by assimilation into the metabolic system of the plant. These auxiliary nutrients further serve as a carrier whereby the compositions of the invention may be suitably applied in a manner that is convenient and precise with regard to rates.

The auxiliary nutrients used in conjunction with the invention comprise ingredients of superior grade in terms of purity and other essential properties. The chemical characteristics of the auxiliary nutrients is dictated by several factors. One factor is the requirement that the applied form of the compositions of the present invention be maintained at a pH of 6.7 or higher to insure the integrity of certain gibberellic acid constituents which are dependent upon the degree of acidity. Another factor is that analytical investigations have shown that the purity of the selected carrier greatly influences the rate of absorption and distribution of nitrogen, phosphate and potassium nutrients by plant tissues.

Based on the aforementioned criteria, the auxiliary nutrients selected for use in association with the growth enhancing compositions of the present invention comprise liquids consisting of photographic grade ammonium thio-sulfate, ammonium polysulfate, 75-85% technical grade phosphoric acid and 45% potassium hydroxide solution; and dry solubles consisting of tri-potassium polyphosphate, potassium phosphates, technical grade diammonium phosphate-ammonium phosphate containing no more than 3% by weight of the impurity tri-calcium phosphate, and feed grade urea of low biuret manufacture.

The growth enhancing compositions of this invention may be formulated for application with an auxiliary nutrient comprising liquid sulfur; nitrogen, phosphate and potassium; and a dry soluble high phosphate, high potassium as the base materials. The essential restriction on the auxiliary nutrient used in the resulting formulation is that the form in which the compositions are applied be maintained at pH levels of 6.7 or higher. This key criteria, together with the requirements of purity and integrity of the present growth enhancing compositions, is virtually assured if the formulation procedure is followed according to a particular sequence. For example, in a liquid sulfur based formulation, $\frac{1}{4}$ parts by weight of liquid ammonium polysulfate are combined with $\frac{3}{4}$ parts by weight of photographic grade ammonium thio-sulfate and the resulting liquid product is then blended with water as the diluent in parts that yield a sulfur content in the range of 14–17.5% by weight. The combined sulfite content of the two liquid sulfates must not exceed $\frac{1}{2}$ of 1%. Utilizing commercially available sources of the two liquid sulfates, the resultant liquid formulation should have a weight per gallon of 9.5–9.75 lbs., which should fall well within the recommended pH levels. It is suggested, however, that the pH be tested on each lot or batch. A suitable amount of the growth enhancing composition of the invention is then fed into the sulfur based diluent with vigorous agitation until thorough dissolution is obtained.

A nitrogen (N), phosphorus (P) and potassium (K) liquid base formulation having 4% by weight nitrogen, 12% by weight phosphorus and 4% by weight potassium or (4-12-4 N-P-K) as the recommended ratio is obtained by feeding water as a diluent into a closed, but vented stainless steel vessel. Next, the proper amount of 75% furnace grade phosphoric acid is mixed into the water, wherein some heat may occur. Approximately one half of the necessary amount of low biuret urea is then added into the solution very slowly to allow heat generated by the occurring reactions to dissipate between additions. The remaining one half of the urea may be added immediately to calm the reaction if it becomes too violent, otherwise the remaining urea and potassium hydroxide are sequentially fed into the vessel to complete the mixing process. Care should be taken in mixing these ingredients since violent reaction and tremendous heat exchange may occur if improper sequences are followed in the mixing process.

After all the ingredients have been properly fed into the vessel, the resultant product is allowed to cool and a clear liquid free of particles and having a pH of 7.0 should be obtained. A pH reading of less than 7.0 indicates the need for slightly more potassium hydroxide, whereas a reading of more than 7.0 indicates the need for slightly more phosphoric acid. When a pH of 7.0 is reached a sufficient amount of the growth enhancing composition of the invention is added and thoroughly mixed. The relatively small quantities of composition added does not effect the pH of the resulting formulation.

The formulation of the liquid compositions of the invention into a soluble high phosphate, high potassium auxiliary powder base may also be obtained by the practice of the present invention to facilitate subsequent precise application of the resulting formulations at recommended rates. First, highly soluble clay granule blanks are auto-claved to reduce the moisture content to a range of 1-3%. These granules are then evenly misted while in a tumbling mixer with a highly concentrated solution of the present growth enhancer in an isopropyl alcohol solvent, wherein the weight of both the granules and growth enhancer are carefully determined. After the granules have been impregnated with alcoholic solution of the growth enhancer, the mixture is placed in a chamber where a low vacuum is applied and the temperature is raised slightly, not to exceed 85° F. Under these conditions, the alcohol solvent quickly evaporates and the dried granules containing the crystalline growth enhancer are milled to a fineness approximating flour in a laboratory type ball mill to produce a highly concentrated soluble powder. The highly concentrated soluble powder is then thoroughly mixed with specific quantities of potassium polyphosphate-potassium phosphate combinations, preferably in a ribbon blender, to increase volume and decrease concentration to a manageable form. The recommended resulting formulation contains 42% by weight of phosphorus (P) and 42% by weight of potassium (K) or a preferred ratio of (0-42-42 P&K).

The precise amount of growth enhancing compositions employed in the practice of the present invention will depend upon the type of response desired, the formulation used and the type of plant species or seed treated. For example, when employed as a seed dressing a preferred rate of from 0.33 to 0.50 gm/acre, based on seedling rates of 14-50 lbs. per acre, of the present compositions applied in conjunction with a (4-12-4 N-P-K) auxiliary nutrient base produces optimum results. For use of the growth enhancer of the invention as a foliar cover spray to balance sulfur:nitrogen ratios and stimulate root development, particularly in nitrogen sensitive crops, or to improve fruit setting in citrus fruits, pears, apples and grapes, optimum rates of from 0.50 to 67 gm/acre are employed. To balance sulfur:nitrogen ratios the present growth enhancer is preferably applied in a liquid sulfur auxiliary nutrient spray and to increase parthenocarpic setting and maturation, phosphate/potassium-based auxiliary nutrient sprays are preferably used. Further, it is preferred that growth enhancers of the present invention be applied at rates of 0.67 to 0.75 gm/acre when employed for the purposes of increasing flowering in a number of economic crops and stimulating regrowth in damaged crops caused by hail, light frost, ect., during early stages of plant development.

The application rate in terms of total volume of formulation used in the practice of this invention may conveniently vary, but must be sufficient to insure that the applied rate of the auxiliary nutrient base delivers the recommended rates of the present growth enhancer to the target crop. For example, if the growth enhancer is applied in a liquid auxiliary nutrient base in the form of an aqueous solution and the desired rate of application is 1 quart per acre of the finished formulation, then the growth enhancing composition of the present invention may be advantageously combined in the formulation in an amount that equals the recommended rate of growth enhancer calculated on a qt/acre basis. The application rate of the finished formulation may be similarly determined on a gallons per acre basis. Thus, the compositions and auxiliary base materials employed in the practice of the present invention may be efficiently mixed at the place of utilization. Also, in view of the relatively low water requirements for the present formulations, the compositions and auxiliary nutrient are obviously advantageous in areas with water deficiency.

The chemical compounds employed as active components of the growth enhancing compositions of the present invention may be prepared in accordance with processes well known in the prior art or may be obtained commercially from ready available sources. It is preferred that the individual chemical compounds be combined in an isopropyl alcohol diluent in the ratios set forth hereinabove, i.e. percentage by weight of the active components, and then formulated into the auxiliary nutrient base in the appropriate amounts.

There will now be presented a number of examples which specifically involve the preferred growth enhancing composition of the present invention, designated hereinabove as "Composition 1", as applied under a variety of application rates and formulations to a variety of plant and seed species in order to induce a number of beneficial responses. Extensive testing in both the controlled environment of the greenhouse and in-field testing has repeatedly verified that the specifically preferred composition applied over exacting rate ranges produces consistent, predictable plant growth responses in most agricultural and other agronomic crops. It can be concluded that the active components of the present composition are quite readily metabolized within the plant tissue to cause an artificial acceleration of the plant's natural life cycle. However, it seems that the composition does more than this because the plant growth enhancing effects of the present invention occur to a greater degree than would be expected to occur in nature. Thus, it would seem to follow that the assimilation of the combination of active components of the invention may trigger the enzymatic or other systems within the plant to produce an unexpected synergistic result.

The foregoing theory is presented in an effort to promote a better understanding of the present invention, although there is no intention to limit the invention to this or any other theory. Other investigations are still being carried out and it is quite possible that additional observations may offer revised explanations. In recognition of this, it is again repeated that the reasons as to why the present invention has proved to be so successful have not as yet been determined with certainty, and this specification is to be so understood.

The following examples are illustrative of the wide range of plant growth responses that can be realized by application of a preferred composition of the present invention to various plant species. Nevertheless, there is no intention that the invention be limited to these optimum ratios of active components since workers in the art will find the compositions of the invention set forth hereinabove to be effective growth enhancers. Also, it should readily occur to one skilled in the art that the recognition of improved results using the compositions according to the present invention in connection with other plants, seeds, fruits and vegetables not specifically illustrated herein is readily within the capabilities of one skilled in the art.

EXAMPLE 1

This evaluation demonstrates the use of the composition of the invention as a wheat seed dressing for stimulating seed germination and increasing vigor.

The experiments were made using a formulation consisting of "Composition 1" as the growth enhancer in association with a (4-12-4 N-P-K) auxiliary base, prepared as set forth hereinabove. All the experiments were run in the summer (August) using wheat seed tagged 80% germination (Caldwell certified). The formulation was applied as a solution in the concentration of 4 fl. oz. per 50 lb. seed, wherein the auxiliary base was formulated to a constant of 8.8 lb./gal.

Four plantings of wheat seeds in separate seeding trays at a depth of 0.5 inches was made using 100 seeds per tray selected at random. Three of the four trays were treated with the growth enhancer at the rate shown in Table 1 and the formulation applied with stirring onto the seeds. The fourth tray, designated herein as the control, was prepared in the exact manner as the other three trays, except that it received no treatment with the growth enhancer (Composition 1). The height of the emerged plants was recorded at the periodic intervals and the following Table shows a comparative summary of the results:

TABLE 1

| Treatment Rate (gm/acre) | Increase Over Control | | |
|---|---|---|---|
| | 3 Days | 5 Days | 7 Days* |
| Control | — | — | — |
| .33 | 20.5% | 23.2% | 19.7% |
| .40 | 28.2% | 26.1% | 22.5% |
| .50 | 35.9% | 23.2% | 19.7% |

*Increase at 7 days is considered the overall increase since no additional plants are reasonably expected to emerge after this period.

The advantageous results of the effect of treatment with the growth enhancer is evident. The treated seeds were quicker to germinate. However, the overall increase in germination of about 20% is the most economically pertinent statistic in this experiment, where hostile conditions were not encountered.

In a similar experiment utilizing the identical formulation described herein, ten plants per trial were selected at random and the plants from both treated and untreated seeding trays were visually inspected 10 days after planting. The height of the inspected plants was recorded and the collected data is shown in the following Table:

TABLE 2

| GROWTH ENHANCER RATE (.33 GRAMS/ACRE) HEIGHT (IN.) | GROWTH ENHANCER RATE (.50 GRAMS/ACRE) HEIGHT (IN.) | CONTROL HEIGHT (IN.) |
|---|---|---|
| 5.500 | 5.625 | 4.250 |
| 5.625 | 5.375 | 5.000 |
| 5.500 | 5.500 | 4.250 |
| 5.125 | 6.000 | 4.500 |
| 5.375 | 5.375 | 4.375 |
| 5.750 | 6.125 | 4.500 |
| 5.000 | 5.375 | 4.375 |
| 5.500 | 5.500 | 4.500 |
| 5.625 | 5.500 | 4.500 |
| 6.250 | 6.000 | 4.250 |

The data from the above Table 2 demonstrates additional growth increments achieved with the growth enhancer of the invention. Excavated plants from both treated and control trays were inspected and show markedly increased root proliferation (size, number and length) in the treated over the untreated control. The results clearly indicates improved vigor and more rapid growth of emerged plants where the growth enhancing composition has been used. A summary of the above data is shown below:

| GROWTH ENHANCER RATE (Grams/Acre) | TREATED (Avg. Ht.) | UN-TREATED (Avg. Ht.) | HEIGHT ADVANTAGE TREATED |
|---|---|---|---|
| .33 | 5.527 in. | 4.426 in. | 24.8% |
| .50 | 5.640 in. | 4.426 in. | 27.4% |

EXAMPLE 2

This evaluation demonstrates the use of the growth enhancer of the invention for stimulating seed breaking of dormancy.

The experiment was conducted using the formulation described in Example 1 in combination with a conventional fungicide. Replicated plantings of peanut seeds in seeding trays were made at a depth of 1.25 inches using 100 seeds per tray. Selected trays were treated with the indicated growth enhancing composition using the recommended rate ranges for seeds, 0.33 to 0.50 grams per acre, and the formulation applied onto the seeds. Other trays were prepared in the exact manner as the treated trays (T), except that they received no treatment with the growth enhancer and these untreated trays were designated as the controls (C). The result are recorded in the Tables below.

TABLE 3

| Tray No. | Emerged 80 hrs. T-C | Emerged 92 hrs. T-C | Emerged 104 hrs. T-C | Emerged 7 days T-C | Emerged 14 days T-C |
|---|---|---|---|---|---|
| 1 | 29-22 | 38-28 | 70-51 | 85-64 | 87-81 |
| 2 | 27-23 | 41-27 | 71-52 | 84-63 | 86-79 |
| 3 | 28-23 | 39-27 | 71-50 | 85-65 | 87-81 |
| 4 | 30-22 | 39-28 | 72-51 | 86-61 | 88-82 |
| 5 | 30-22 | 39-28 | 68-52 | 86-61 | 89-82 |
| 6 | 30-22 | 38-27 | 70-51 | 85-63 | 86-78 |
| 7 | 26-61 | 38-26 | 68-51 | 86-64 | 88-81 |
| 8 | 29-24 | 40-27 | 68-54 | 84-64 | 86-80 |
| 9 | 29-25 | 37-27 | 69-50 | 86-64 | 88-82 |
| 10 | 32-26 | 38-27 | 71-51 | 85-64 | 86-80 |
| 11 | 31-25 | 36-28 | 70-54 | 86-65 | 88-81 |
| 12 | 29-23 | 35-29 | 71-51 | 84-66 | 88-81 |
| 13 | 31-23 | 38-28 | 71-50 | 86-64 | 88-81 |
| 14 | 28-22 | 38-28 | 72-49 | 85-61 | 87-79 |
| 15 | 29-22 | 37-27 | 71-51 | 86-66 | 87-79 |
| 16 | 31-22 | 39-27 | 71-50 | 86-61 | 88-81 |
| 17 | 30-23 | 39-28 | 71-49 | 81-66 | 85-78 |
| 18 | 27-24 | 39-26 | 72-51 | 84-65 | 87-80 |
| 19 | 29-22 | 40-28 | 71-50 | 84-65 | 86-79 |
| 20 | 30-22 | 41-29 | 72-51 | 86-65 | 88-81 |

TABLE 4

| Tray No. | Emerged 80 hrs. T-C | Emerged 92 hrs. T-C | Emerged 104 hrs. T-C | Emerged 7 days T-C | Emerged 14 days T-C |
|---|---|---|---|---|---|
| 1 | 32-23 | 39-28 | 73-53 | 86-67 | 86-80 |
| 2 | 31-24 | 41-28 | 71-53 | 86-65 | 86-78 |
| 3 | 33-24 | 40-29 | 71-50 | 85-65 | 86-84 |
| 4 | 34-25 | 38-31 | 70-51 | 84-65 | 86-84 |
| 5 | 32-25 | 39-32 | 72-51 | 79-61 | 86-84 |
| 6 | 33-24 | 37-30 | 72-52 | 85-63 | 84-81 |
| 7 | 31-24 | 40-28 | 71-50 | 85-64 | 85-83 |
| 8 | 31-25 | 40-29 | 73-51 | 84-65 | 85-83 |
| 9 | 32-25 | 39-28 | 69-51 | 86-65 | 85-83 |
| 10 | 32-23 | 38-27 | 70-51 | 86-63 | 87-81 |
| 11 | 32-24 | 39-27 | 71-50 | 86-60 | 86-83 |
| 12 | 31-25 | 37-28 | 71-50 | 85-66 | 86-83 |
| 13 | 32-26 | 37-29 | 74-50 | 84-66 | 85-80 |
| 14 | 33-23 | 37-28 | 72-52 | 83-60 | 84-83 |
| 15 | 31-24 | 38-31 | 74-51 | 83-54 | 86-83 |
| 16 | 32-24 | 39-31 | 72-51 | 83-61 | 86-81 |
| 17 | 31-23 | 40-30 | 72-54 | 86-62 | 87-83 |
| 18 | 32-25 | 41-28 | 71-51 | 87-63 | 85-83 |
| 19 | 31-24 | 39-29 | 73-52 | 84-63 | 85-81 |

TABLE 4-continued

| Tray No. | Emerged 80 hrs. T-C | Emerged 92 hrs. T-C | Emerged 104 hrs. T-C | Emerged 7 days T-C | Emerged 14 days T-C |
|---|---|---|---|---|---|
| 20 | 32-23 | 38-30 | 72-51 | 86-59 | 85-81 |

Soil temperatures were held at a constant 68° F. in the treatments set forth in Table 3 and the soil temperatures in the treatments of Table 4 were held at 72° F. It should be noted that there is little difference between the 68 and 72 degrees at 7 days on the treated seed, while there was a marked difference in the germination rate of the untreated seeds with a 4 degree variable. At 14 days, the 4 degree differential made little difference in the net result of treated compared to treated, and control compared to control. There was, however, a wide gap between the germination rate of treated versus control trays. This substantiates postulations of the initiation of dormancy break by the growth enhancer of the invention under lower than normal temperatures or adverse hostile conditions in the field.

The results of the experiments set forth in Tables 3 and 4 are summarized below.

|  | EMERGED 80 Hrs. T-C | EMERGED 92 Hrs. T-C | EMERGED 104 Hrs. T-C | EMERGED 7 days T-C | EMERGED 14 days T-C |
|---|---|---|---|---|---|
| Table 3 (Total) | .29-.23 | .39-.28 | .71-.51 | .85-.64 | .87-.81 |
| Table 4 (Total) | .33-.25 | .44-.32 | .75-.55 | .85-.73 | .87-.82 |
| TOTALS-TREATED | 62 | 83 | 146 | 170 | 170 |
| TOTALS-CONTROL | 48 | 60 | 96 | 137 | 163 |
| AVERAGE TREATED | 31% | 42% | 73% | 85% | 87% |
| AVERAGE CONTROL | 24% | 30% | 48% | 68% | 81% |

As indicated above the growth enhancing composition repeatedly exhibited the ability to cause the planting seed to break dormancy much more quickly than would be normal. Also, the dormancy break is more even than would be experienced under usual field conditions. This characteristic is especially important in crops such as peanuts, where germination and emergence may normally take place over as much as three weeks. Peanuts treated with the composition of this invention emerge more quickly and evenly than do untreated peanut seed. On an average peanut seeds treated with the present composition emerge to an acceptable stand within 7-8 days after planting, or in a minimum of one-half the usual time.

Other experiments conducted under conditions similar to those hereinabove demonstrated the use of the composition of the present invention in inducing freeze resistance. Specifically, shortly after planting, within 36 hours, the temperature fell to below 40° F. Treated seed was fully emerged within 7 days and showed little, if any, cold shock after emergence. Untreated seed failed to come up at all.

EXAMPLE 3

This evaluation demonstrates the use of the composition of the invention for increasing the dry weight content of shoot and root growth in various plants.

The experiments were conducted using the formulation and general procedure set forth in Example 1. The formulation had a concentration of 0.33 grams of the plant growth enhancing composition per 4 fl. oz. of the auxiliary nutrient base (4-12-4 N-P-K). The liquid formulation was applied to the seed at the rate of 4 fl. oz. per 14 lbs. of cotton seed and 4 fl. oz. per 50 lbs. of soybean seed. The results are recorded in the Tables below.

TABLE 5

The Effect of Test Formulations on Growth of Soybeans at 8 Days

| Treatment | Dry Weight* | | | Shoot-Root Ratio |
|---|---|---|---|---|
|  | Shoot | Root | Total |  |
| Control |  |  |  |  |
| 1 | .825 | .258 | 1.083 | 3.19 |
| 2 | .807 | .234 | 1.041 | 3.45 |
| 3 | .934 | .236 | 1.170 | 1.44 |
| 4 | .992 | .298 | 1.290 | 3.56 |
| 5 | .990 | .234 | 1.224 | 4.23 |
| 6 | 1.056 | .238 | 1.294 | 4.43 |
| 7 | 1.070 | .292 | 1.362 | 3.66 |

*Total for ten representative seedlings recorded in grams.

TABLE 6

The Effect of Test Formulations on Growth of Cotton at 8 Days

| Treatment | Dry Weight* | | | Shoot-Root Ratio |
|---|---|---|---|---|
|  | Shoot | Root | Total |  |
| Control |  |  |  |  |
| 1 | .501 | .118 | .619 | 4.25 |
| 2 | .428 | .067 | .495 | 6.38 |
| 3 | .486 | .087 | .573 | 5.59 |
| 4 | .697 | .083 | .780 | 8.40 |
| 5 | .578 | .091 | .669 | 6.35 |
| 6 | .529 | .072 | .601 | 7.35 |
| 7 | .541 | .065 | .606 | 8.32 |

*Total for ten representative seedlings recorded in grams.

TABLE 7

The Effect of Test Formulations on Growth of Soybeans at 10 Days

| Treatment | Dry Weight* | | | Shoot-Root Ratio |
|---|---|---|---|---|
|  | Shoot | Root | Total |  |
| Control |  |  |  |  |
| 1 | .873 | .363 | 1.236 | 2.40 |
| 2 | 1.002 | .265 | 1.267 | 3.78 |
| 3 | .982 | .270 | 1.252 | 3.63 |
| 4 | .980 | .234 | 1.214 | 4.18 |
| 5 | .888 | .399 | 1.287 | 2.23 |
| 6 | 1.202 | .274 | 1.476 | 4.39 |
| 7 | .994 | .268 | 1.262 | 3.70 |

*Total for ten representative seedlings recorded in grams.

TABLE 8

Effect of Test Formulations on Selected Cotton Growth Parameters

| Treatment | Shoot Length (cm) | Root Length (cm) | Shoot-Root Ratio | Leaf Area |
|---|---|---|---|---|
| Control |  |  |  |  |
| 1 | 70 | 175 | .40 | 100% |
| 2 | 78 | 87 | .90 | 138% |
| 3 | 75 | 164 | .46 | 126% |
| 4 | 62 | 163 | .38 | 112% |
| 5 | 98 | 168 | .58 | 149% |
| 6 | 80 | 108 | .74 | 151% |

TABLE 8-continued

Effect of Test Formulations on Selected Cotton Growth Parameters

| Treatment | Shoot Length (cm) | Root Length (cm) | Shoot-Root Ratio | Leaf Area |
|---|---|---|---|---|
| 7 | 82 | 117 | .70 | 162% |

TABLE 9

Effect of Test Formulations on Selected Cotton Growth Parameters

| Treatment | Shoot Length (cm) | Root Length (cm) | Shoot-Root Ratio | Leaf Area |
|---|---|---|---|---|
| Control | | | | |
| 1 | 118 | 263 | .45 | 100% |
| 2 | 138 | 263 | .52 | 131% |
| 3 | 168 | 248 | .68 | 135% |
| 4 | 177 | 312 | .57 | 132% |
| 5 | 140 | 215 | .65 | 78% |
| 6 | 187 | 280 | .67 | 155% |
| 7 | 139 | 215 | .65 | 86% |

TABLE 10

Effect of Test Formulations on Soybean Seed Germination*

| Treatment | Day 1 | 2 | 3 | 4 | 5 | 6 | 7 |
|---|---|---|---|---|---|---|---|
| Control | | | | | | | |
| 1 | 0 | 0 | 20 | 86 | 100 | 97 | |
| 2 | 0 | 35 | 84 | 87 | 90 | 90 | |
| 3 | 0 | 0 | 82 | 96 | 96 | 94 | |
| 4 | 0 | 0 | 95 | 97 | 98 | 98 | |
| 5 | 0 | 11 | 78 | 91 | 92 | 95 | |
| 6 | 0 | 3 | 90 | 98 | 99 | 92 | |
| 7 | 0 | 3 | 24 | 87 | 88 | 91 | |

TABLE 11

Effect of Test Formulations on Cotton Seed Germination*

| Treatment | Day 1 | 2 | 3 | 4 | 5 | 6 | 7 |
|---|---|---|---|---|---|---|---|
| Control | | | | | | | |
| 1 | 0 | 1 | 4 | 75 | 86 | | |
| 2 | 0 | 4 | 9 | 58 | 75 | | |
| 3 | 0 | 0 | 0 | 70 | 82 | | |
| 4 | 0 | 0 | 0 | 40 | 67 | | |
| 5 | 0 | 0 | 0 | 53 | 77 | | |
| 6 | 0 | 0 | 0 | 69 | 86 | | |
| 7 | 0 | 0 | 0 | 66 | 77 | | |

*Rated as emergence; data is percent germination of 100 seeds in soil, in greenhouse trials.

The above tests clearly indicate the overall growth and development of plants achieved with the compositions of the present invention. The treated seed produced plants having heavier stems and appreciably more lateral shoots than the controls. The effects are desirable in that firmer and stronger plants reduce lodging and give greater crop bearing vegetation.

EXAMPLE 4

This evaluation demonstrates the use of the composition of the invention for increasing yield.

The experiments were conducted using a formulation consisting of "Composition 1" as the growth enhancer in conjunction with the liquid sulfur auxiliary nutrient base, prepared in accordance with the method specifically described hereinabove. The formulation had a concentration of 2.0 grams of the growth enhancer per gallon of the sulfur nutrient base and was applied to a field at a rate of 1 quart per acre. This rate directly corresponds to the recommended rate of 0.50 grams of the active growth enhancing composition per acre. The experiments were run in the winter (December–January) in a field environment.

The formulation was applied to an area of the field planted with corn seed, while the remainder of the planted field was untreated. Corn was harvested from various areas within both plots and an average of 15 ears were found within each area. The total ear weights were determined then shuck, kernel and cob were separated. The individual kernel and cob weights were determined and converted to lbs./acre. The results are recorded below, wherein the numerical values are set forth in lbs./acre.

TABLE 12

| | I | II | III | IV | MEAN | % INCREASE |
|---|---|---|---|---|---|---|
| TREATED PRODUCT | | | | | | |
| Total Ear | 4838 | 4805 | 4851 | 4840 | 4833 | 9.1 |
| Kernel | 3400 | 3410 | 3379 | 3392 | 3395 | 10.5 |
| Cob | 964 | 975 | 981 | 996 | 979 | 11.6 |
| UNTREATED CONTROL | | | | | | |
| Total Ear | 4398 | 4402 | 4430 | 4493 | 4431 | |
| Kernel | 3091 | 3070 | 3035 | 3087 | 3071 | |
| Cob | 876 | 880 | 891 | 862 | 877 | |

Even though the above test was conducted under adverse field conditions, treatment of seed corn with a composition of the invention is of significant economic value for increasing the actual yield of the crop.

The results set forth above fully illustrate the wide variety of plant growth enhancing responses achieved by the present invention. Similar experiments with various other plant species indicate that similar results can be attained by such treatments on a wide variety of plants. Therefore, those skilled in the art may find the compositions of the present invention to be an effective growth enhancer on other plant species. Also, various changes and modifications can be made without departing from the spirit of invention. Accordingly, the foregoing illustrations are not to be interpreted as restrictive of the invention beyond that necessitated by the following claims.

We claim:

1. A composition for enhancing the growth of plants comprising a growth enhancing effective amount of a mixture of:
   (a) 35–45 percent by weight of gibberellins,
   (b) 35–45 percent by weight of indole-3-acetic acid, and
   (c) 15–25 percent by weight of 6-(4-hydroxy-3-methyl-2-trans-betenylamino) purine.

2. The composition according to claim 1 wherein said composition comprises about 40 percent by weight of gibberellins, about 40 percent by weight of indole-3-acetic acid and about 20 percent by weight of 6-(4-hydroxy-3-methyl-2-trans-betenylamino) purine.

3. The composition according to claim 2 wherein said gibberellins are a mixture of gibberellic acids consisting of gibberellin $A_2$, gibberellin $A_3$, gibberellin $A_5$, gibberellin $A_7$ and gibberellin $A_{14}$.

4. The composition according to claim 3 wherein said mixture of gibberellic acids consists of 4% by weight gibberellin $A_2$, 76% by weight gibberellin $A_3$, 4% by weight gibberellin $A_5$, 4% by weight gibberellin $A_7$ and 12% by weight gibberellin $A_{14}$.

5. A composition for enhancing the growth of plants consisting essentially of a growth enhancing effective amount of a mixture of:
(a) 40.3 percent by weight of a mixture of gibberellic acids consisting of 4% by weight gibberellin $A_2$, 76% by weight gibberellin $A_3$, 4% by weight gibberellin $A_5$, 4% by weight gibberellin $A_7$ and 12% by weight gibberellin $A_{14}$,
(b) 38.7 percent by weight of indole-3-acetic acid, and
(c) 21 percent by weight of 6-(4-hydroxy-3-methyl-2-trans-betenylamino) purine.

6. A method for enhancing the growth of a plant which comprises applying to the plant, locus of the plant or to the seeds of the plant, a plant growth enhancing effective amount of a composition according to claim 1.

7. The method according to claim 6 wherein the composition is applied as a seed dressing to the seeds of a plant at a rate of 0.33 to 0.50 grams per acre based on seedling rates of 14 to 50 lbs. per acre.

8. The method according to claim 6 wherein the composition is applied as a foliar cover spray to the plant at a rate of 0.50 to 0.75 grams per acre.

9. The method according to claim 6 wherein the composition is applied in the form of a liquid solution having a pH of 6.7 or higher.

10. The method according to claim 6 wherein the composition is in the form of a soluble powder.

11. The method according to claim 7 wherein the composition is applied as a liquid formulation at a rate equal to 4 fl. oz. per 50 lbs. of seeds.

12. The method according to claim 11 wherein the total concentration of said composition in said liquid formulation is 0.33 grams per 4 fl. oz.

13. A method of enhancing the growth of a plant which comprises applying to the plant or the seeds of the plant a growth enhancing effective amount of a composition according to claim 5.

* * * * *